(12) United States Patent
Perraut et al.

(10) Patent No.: US 10,458,897 B2
(45) Date of Patent: Oct. 29, 2019

(54) METHOD FOR IDENTIFYING BIOLOGICAL PARTICLES USING STACKS OF DEFOCUSED HOLOGRAPHIC IMAGES

(71) Applicants: COMMISSARIAT A L'ENERGIE ATOMIQUE ET AUX ENERGIES ALTERNATIVES, Paris (FR); BIOMERIEUX, Marcy-l'Etoile (FR)

(72) Inventors: Francois Perraut, Saint Joseph de Riviere (FR); Pierre Joly, Grenoble (FR); Quentin Josso, Lyons (FR); Meike Kloster-Landsberg, Grafelfing (DE); Alice Douet, Grenoble (FR)

(73) Assignees: COMMISSARIAT A L'ENERGIE ATOMIQUE ET AUX ENERGIES ALTERNATIVES, Paris (FR); BIOMERIEUX, Marcy-l'Etoile (FR)

( * ) Notice: Subject to any disclaimer, the term of this patent is extended or adjusted under 35 U.S.C. 154(b) by 152 days.

(21) Appl. No.: 15/536,507

(22) PCT Filed: Dec. 17, 2015

(86) PCT No.: PCT/EP2015/080148
§ 371 (c)(1),
(2) Date: Jun. 15, 2017

(87) PCT Pub. No.: WO2016/097092
PCT Pub. Date: Jun. 23, 2016

(65) Prior Publication Data
US 2017/0284926 A1    Oct. 5, 2017

(30) Foreign Application Priority Data
Dec. 19, 2014  (FR) ...................................... 14 62998

(51) Int. Cl.
*G01N 15/14*     (2006.01)
*G03H 1/00*      (2006.01)
(Continued)

(52) U.S. Cl.
CPC ....... *G01N 15/1475* (2013.01); *G03H 1/0005* (2013.01); *G03H 1/0443* (2013.01);
(Continued)

(58) Field of Classification Search
None
See application file for complete search history.

(56) References Cited

U.S. PATENT DOCUMENTS 6,496,262 B1 * 12/2002 Meng ...................... G01P 5/001
                                                356/339
2013/0280752 A1 * 10/2013 Ozcan ................ G01N 21/4795
                                                435/29
(Continued)

FOREIGN PATENT DOCUMENTS

DE    10 2005 036 326 A    2/2007
WO    WO 2013/041951 A1    3/2013

OTHER PUBLICATIONS

International Patent Application Publication No. WO 2013/041951 (Year: 2013).*

(Continued)

*Primary Examiner* — Soo Shin
(74) *Attorney, Agent, or Firm* — Oblon, McClelland, Maier & Neustadt, L.L.P.

(57) ABSTRACT

The invention concerns a method for identifying biological particles from a stack of holographic images obtained by means of an optical system. A stack of image blocks centered on the biological particle to be analysed is extracted from the stack of images and a reference block corresponding to the focus plan is determined. A characteristic magnitude is calculated for each block of the stack and the profile of this characteristic magnitude along the optical axis of the system is compared with a plurality of standard profiles relative to known types of particle. Alternatively, blocks of the stack are extracted from the stack of blocks for predetermined defocusing deviations and the extracted blocks are compared with standard blocks relative to known types of particle.

16 Claims, 6 Drawing Sheets

(51) Int. Cl.
G03H 1/04 (2006.01)
G03H 1/08 (2006.01)
G06K 9/00 (2006.01)

(52) U.S. Cl.
CPC ....... *G03H 1/0866* (2013.01); *G06K 9/00147* (2013.01); *G01N 2015/1445* (2013.01); *G03H 2001/005* (2013.01); *G03H 2001/0883* (2013.01)

(56) References Cited

U.S. PATENT DOCUMENTS

2014/0205176 A1 7/2014 Obrien et al.
2017/0220000 A1* 8/2017 Ozcan ................. G03H 1/0866
2018/0144182 A1* 5/2018 El-Zehiry .......... G01N 15/1463

OTHER PUBLICATIONS

Lee et al., "Holographic Microscopy of holographically trapped three-dimensional structures," Opt. Express 15(4), 1505-1512 (2007) (Year: 2007).*

Kim, "Advances and applications on micro-defocusing digital particle image velocimetry (μ-DDPIV) techniques for microfluidics," Journal of Mechanical Science and Technology 26 (12) (2012) 3769-3784 (Year: 2012).*

International Search Report dated Feb. 15, 2016 in PCT/EP2015/080148, filed Dec. 17, 2015.

French Search Report dated Sep. 4, 2015 in 1462998, filed Dec. 19, 2014.

Sang-Hyuk Lee et al. "Holographic microscopy of holographically trapped three-dimensional structures", Optics Express, vol. 15, No. 4, Feb. 19, 2007 pp. 1505-1512.

Myung K. Kim "Principles and techniques of digital holographic microscopy", SPIE Reviews, vol. 1, 2010, 51 pages.

Ahmed El Mallahi et al. "Automated three-dimensional detection and classification of living organisms using digital holographic microscopy with partial spatial coherent source: application to the monitoring of drinking water resources", Applied Optics, vol. 52, No. 1, Jan. 1, 2013, pp. A68-A80.

N. Wu, et al., "Three-Dimensional Identification of Microorganisms Using a Digital Holographic Microscope," Computational and Mathematical Methods in Medicine, vol. 2013, 2013, 7 pages.

U.S. Appl. No. 15/526,092, filed May 11, 2017, Francois Perraut et al.

* cited by examiner

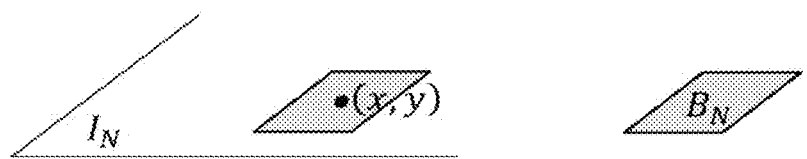
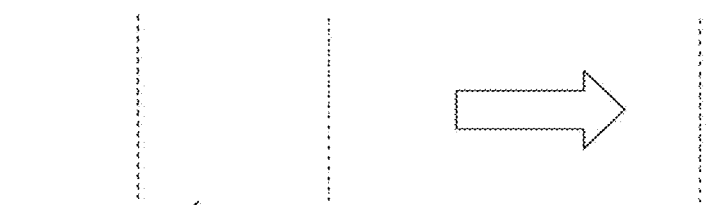
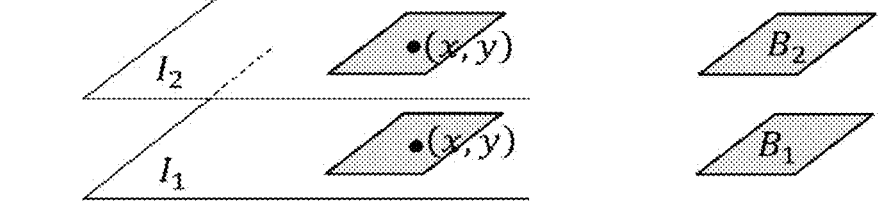
Fig. 3
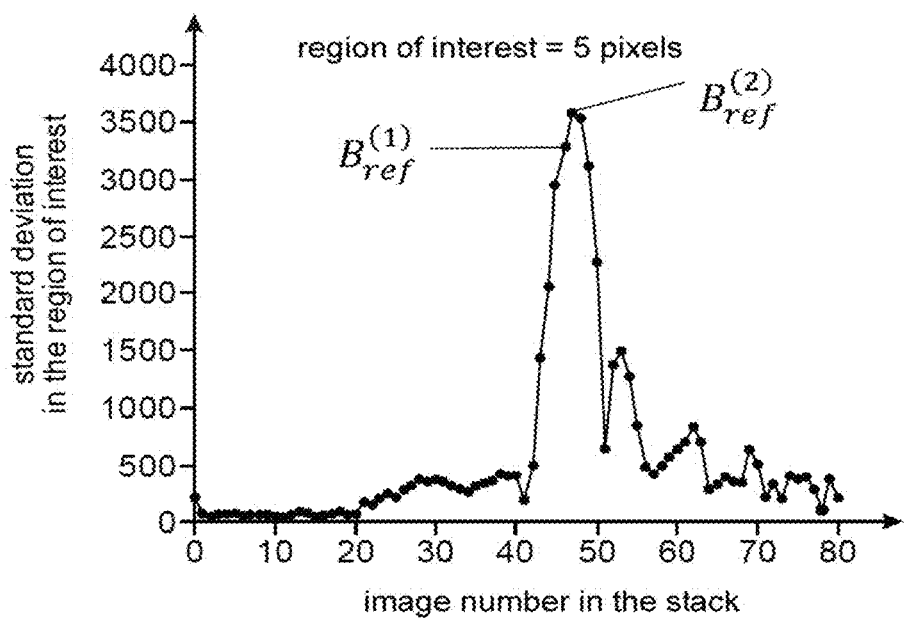
Fig. 4

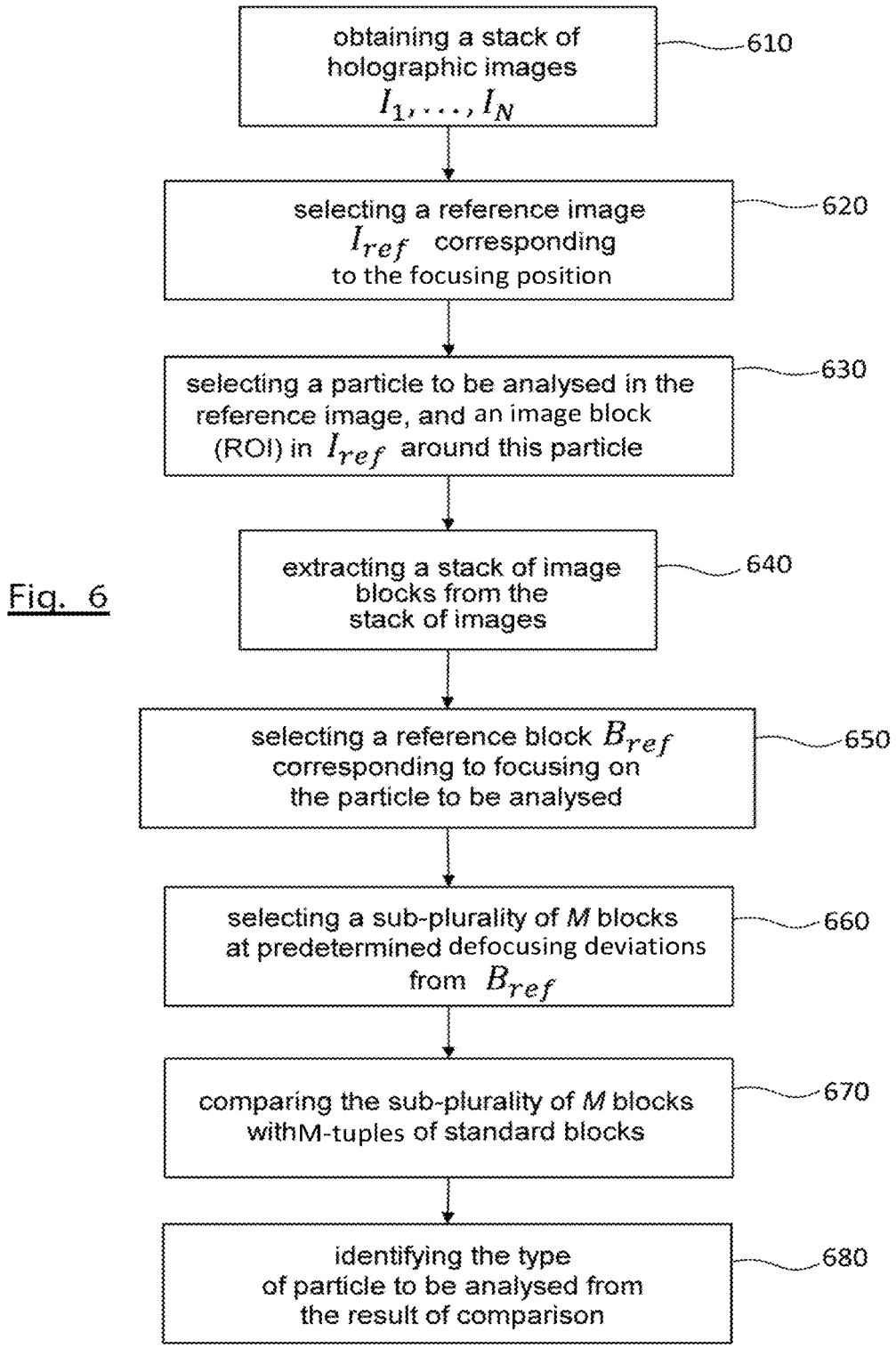

METHOD FOR IDENTIFYING BIOLOGICAL PARTICLES USING STACKS OF DEFOCUSED HOLOGRAPHIC IMAGES

TECHNICAL FIELD

The present invention generally concerns the field of the optical analysis of biological particles. It particularly finds application to microbiological diagnosis, and more particularly to the identification of microorganisms and/or their stress response condition. It can also be applied to the monitoring of cell cultures.

BACKGROUND ART

Digital Holographic Microscopy, DHM, is a known imaging technique allowing field depth constraints of conventional optical microscopy to be overcome. Schematically, it consists of recording a hologram formed by interference between the light waves diffracted by the observed object and a reference wave having spatial coherence. A general introduction to digital holographic microscopy can be found in the article by Myung K. Kim titled « Principles and techniques of digital holographic microscopy » published in SPIE Reviews Vol. 1, N° 1, January 2010.

It has recently been proposed to use digital holographic microscopy for automated identification of microorganisms. For example, the article by N. Wu et al. titled « Three-dimensional identification of microorganisms using a digital holographic microscope » published in Computational and Mathematical Methods in Medicine, Vol. 2013, art. No. ID 162105, describes a method to identify different types of bacteria in a volume to be analysed by means of numerical propagation towards the plane corresponding to a focus on the particle. The images focused at different depths are used to reconstitute a three-dimensional representation of the microorganisms. These are then classified using non-linear 3D filtering.

Similarly, the article by Ahmed El Mallahi titled « Automated three-dimensional detection and classification of living organisms using digital holography microscopy with partial spatial coherent source: application to monitoring of drinking water resources » published in Applied Optics, Vol. 52 No. 1, January 2013, describes a method comprising a first step to detect the position of the bacteria in the volume to be analysed, a focusing step at different depths in the volume using numerical propagation, followed by classification of the bacteria from their morphological characteristics.

The aforementioned identification methods are complex, however, insofar as they require focusing in successive focus planes. A contrario, focusing in a single focus plane, in other words at a single analysis depth, is generally insufficient for the identification of a type of microorganism with low false detection rate. It is therefore the objective of the invention to propose a method for identifying organic particles by digital holographic microscopy which allows a low false detection rate to be obtained whilst being simple and robust.

SUMMARY OF THE INVENTION

The present invention is defined by a method for identifying biological particles from a stack of holographic images obtained using an optical system, wherein:

said holographic images are obtained for a plurality of defocusing deviations relative to a focus plane, the defocusing deviations being taken along the optical axis of the optical system;
a reference holographic image is selected in the stack of holographic images as being the closest to a focus plane;
for a biological particle of interest, a stack of image blocks comprising said biological particle of interest is extracted from the stack of holographic images;
the type of the particle of interest is identified from the extracted stack of image blocks.

A minimum defocusing deviation is preferably greater than a maximum thickness of the biological particle of interest, so that the image blocks comprise no more than a single focused image of the biological particle of interest.

According to a first variant of embodiment, the holographic images are acquired by the optical system for a plurality of positions along the optical axis.

According to a second variant of embodiment, a holographic image is acquired by the optical system and the other holographic images of the stack of holographic images are calculated from the first holographic image using a numerical propagation model. In this case, the first holographic image is advantageously taken with nonzero defocusing deviation relative to the focus plane.

Said reference image can be selected from the stack of holographic images as the image which maximises a predetermined contrast criterion.

Next a reference block is selected in the stack of image blocks, as the image block that is centred on the particle of interest and that belongs to the reference image, the position of the reference block on the optical axis then being selected as origin for the defocusing deviations.

The reference block can then be updated by searching - among the image blocks centred on the particle of interest and belonging to neighbouring images of the reference image in the stack of holographic images - for the image that maximises a predetermined contrast criterion.

According to a first embodiment, for each block of the stack of image blocks, the value is calculated of at least one characteristic magnitude on this block and a profile of said characteristic magnitude is obtained along the optical axis from the values of the characteristic magnitude thus calculated.

The profile of said characteristic magnitude is then compared with a threshold and it is inferred that the biological particle of interest is of a first type if this profile exceeds this threshold and of a second type if does not exceed this threshold.

Alternatively, using a similarity criterion, the profile of said characteristic magnitude is compared with a plurality of standard profiles obtained for different known types of biological particles, and the type of biological particle is inferred from the standard profile having the greatest similarity with the profile of said characteristic magnitude.

The similarity criterion can be selected from among an intercorrelation, a Pearson coefficient, a quadratic deviation.

Further alternatively, the profile of said characteristic magnitude is classified using a supervised learning method among a plurality of classes of profiles, each class corresponding to a given type of biological particle.

According to a second embodiment a plurality of blocks is selected in said stack of image blocks, corresponding to predetermined defocusing deviations.

A comparison is then performed, using a similarity criterion, between said plurality of selected blocks and same pluralities of standard blocks, each plurality of standard blocks corresponding to a given type of biological particle, the type of the biological particle of interest being inferred from the plurality of standard blocks having the greatest similarity with said plurality of selected blocks.

The similarity criterion here too may be an intercorrelation, a quadratic deviation, quadratic deviation after spatial Fourier transform, a criterion based on principal component analysis.

BRIEF DESCRIPTION OF THE DRAWINGS

Other characteristics and advantages of the invention will become apparent on reading preferred embodiments with reference to the appended Figures among which:

FIG. 3 schematically illustrates the extraction of a stack of image blocks from a stack of images;

FIG. 4 schematically illustrates the search for a reference block in a stack of blocks;

FIG. 6 schematically illustrates a flowchart of the method for identifying biological particles according to a second embodiment of the invention;

DETAILED DESCRIPTION OF PARTICULAR EMBODIMENTS

Figure 1:
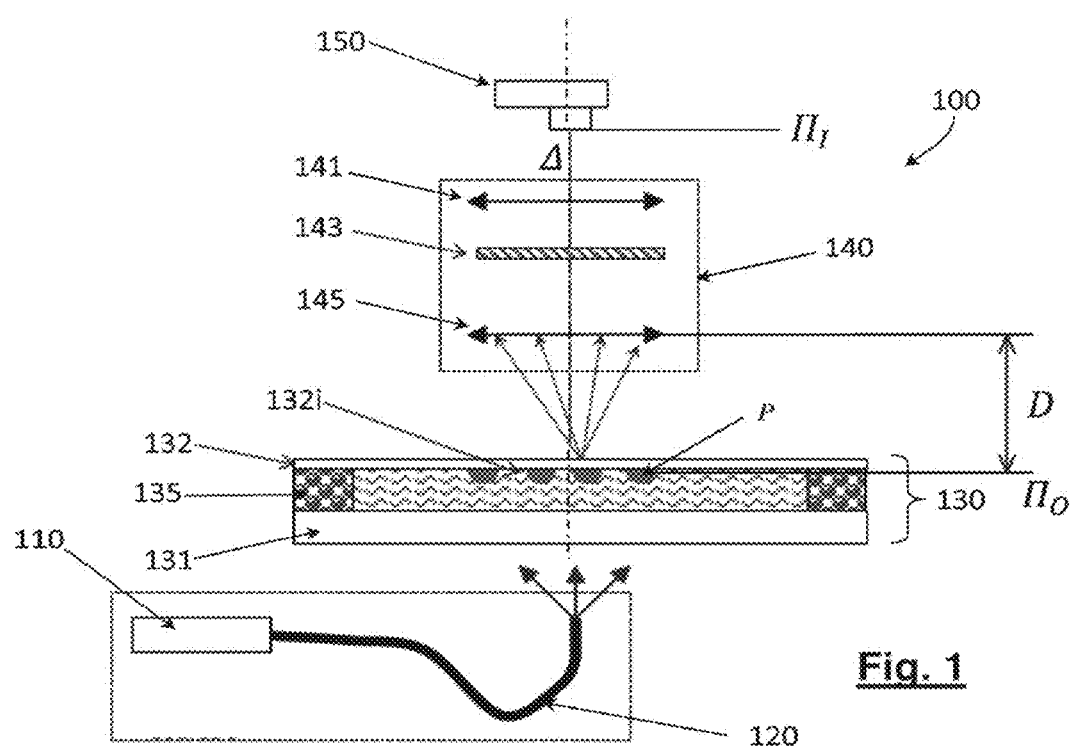
FIG. 1 schematically illustrates a device for recording holographic images that can be used in the method of the invention for identifying biological particles.

The method of the invention for identifying biological particles has recourse to a device for recording holographic images such as the one described in connection with FIG. 1.

This device, 100, comprises a light source, 110, preferably temporally coherent, of narrow spectral width e.g. less than 200 nm or even 100 nm, or even less than 25 nm. This light source may be a laser diode in particular, or a light emitting diode. The light source is preferably spatially coherent. The light beam emitted by the source is conveyed by an optical fibre underneath the sample to be analysed 120. This sample is a liquid such as water, a buffer solution, a culture medium or reactive medium containing biological particles, P, to be identified. Alternatively, the sample may be in the form of a solid medium, preferably transparent, such as an agar containing the particles under consideration. The sample may also be a gaseous medium. The biological particles may be contained inside the medium or on the surface of the sample.

The biological particles to be identified may be microorganisms such as bacteria or yeasts for example. They may also be cells, multicell organisms or any other particle of type polluting or dust particle.

The size of the observed particles varies between 100 nm and several hundred μm, even a few millimeters.

The sample is enclosed in an analysis chamber, 130, vertically delimited by a lower slide 131, e.g. a conventional microscope slide, and an upper slide 132. The analysis chamber is laterally delimited by an adhesive 135 or any other impervious material. The lower and upper slides are transparent to the wavelength of the light source. The biological particles are immobilised in the chamber either because the medium in which they are contained is solid (agar) or because the medium is fluid but the particles attach to the inner surface 132i of the upper slide. The particles may be mobile provided that their speed of motion is sufficiently slow so that the particles are able to be considered immobile during the measuring time.

The device 100 further comprises an optical system 140, formed for example of a microscope objective lens 145 and tube lens 141. The optical system is optionally equipped with a filter 143 which may be positioned in front of the objective lens or between the objective lens and tube lens.

The optical system 140 is characterized inter alia by its optical axis Δ, object plane, or focus plan, at a distance D from the objective lens, and its image plane $\Pi_I$, conjugate of the object plane by the optical system. In other words, for an object lying in the object plane $\Pi_O$, there is a corresponding sharp image of this object in the image plane, $\Pi_I$. The object and image planes are orthogonal to the optical axis Δ.

An image sensor, 150, e.g. a CCD or CMOS sensor is positioned in the image plane $\Pi_I$, or in the vicinity thereof. Therefore, the sensor 150 acquires an image by transmission of a portion of the focus plane.

The position of the optical system 140 relative to the analysis chamber 130 can be vertically adjusted. For example, the objective lens is secured to a lens holder able to be moved along a vertical rail. It is therefore possible to focus on one or more biological particles of interest.

The image formed on the image sensor is a holographic image since it results from interference between a wave diffracted by the biological particles and a reference wave which has passed through the sample without interacting therewith.

Alternatively, it is possible to split the light beam into two components, e.g. using a semi-transparent plate (not illustrated). The first component then acts as reference wave and the second component is diffracted by the sample, the image in the image plane of the optical system resulting from interference between the diffracted wave and reference wave.

The images of the sample thus acquired are then processed using the identification method of the invention.

Figure 2:
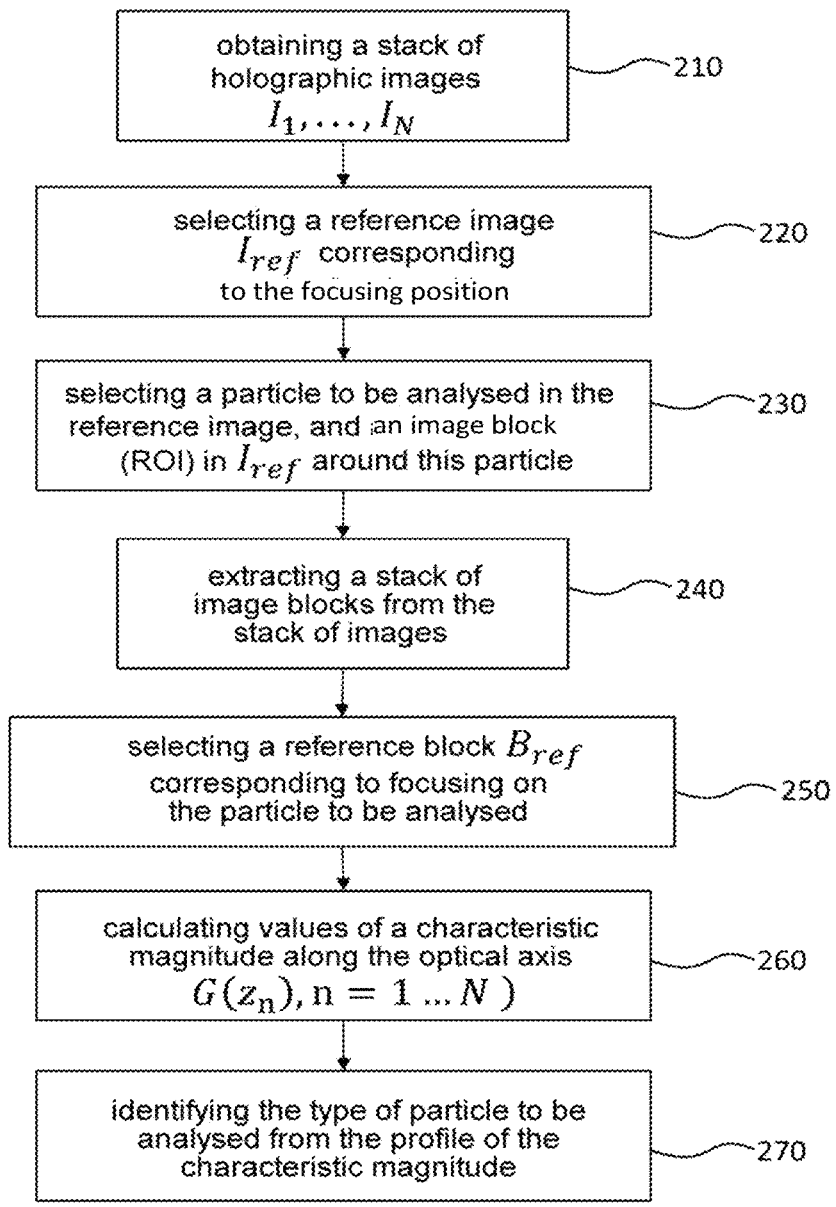
FIG. 2 schematically illustrates a flowchart of the method for identifying biological particles according to a first embodiment of the invention.

FIG. 2 schematically illustrates a flowchart of the method for identifying biological particles according to a first embodiment of the invention.

At step 210, a plurality (or stack) of holographic images is obtained of the biological particles of interest in a sample.

According to a first variant, these images are experimentally acquired by the imaging system, each of these images corresponding to different distances from the analysis chamber taken along the optical axis Δ.

According to a second variant, a first image is acquired at a first distance from the analysis chamber, this distance not necessarily corresponding to focusing conditions on these particles. In particular, it is to be noted that when the biological particles to be analysed are transparent to the wavelength of the source, this first image will not be taken under focusing conditions but at a predetermined distance from the focusing position. This distance is preferably shorter than 2 mm, more preferably shorter than 1 mm, even 500 μm. This first image thus acquired is then said to be defocused.

Additional images are calculated from an initial defocused image, using a numerical propagation model as explained below. The calculated additional images are those which would be observed at different distances between the optical system and the analysis chamber i.e. at different axial positions of the imaging system.

The image computing method by numerical propagation is explained in the article by Sang-Hyuk Lee et al. titled «Holographic microscopy of holographically trapped three-dimensional structures» published in Optics Express, Vol. 15; No. 4, 19 Feb. 2007, pp. 1505-1512.

More specifically, if the propagation function of Rayleigh-Sommerfeld is denoted $h_z(r)$, i.e.:

$$h_z(r) = -\frac{1}{2\pi}\frac{\partial}{\partial z}\frac{e^{ikR}}{R} \quad (1)$$

where z is the defocusing height, in other words the deviation from the focus plane, $r=(x,y)$ is the position in the image plane, $R^2=r^2+z^2$ and $k=2\pi n/\lambda$ is the wave number relative to the propagation medium, then the wave in the plane of ordinate z can be expressed in the form:

$$a(r, z) = |a(r, z)|\exp(i\varphi(r, z)) \quad (2\text{-}1)$$

$$a(r, z) = \frac{1}{4\pi^2}\int_{-\infty}^{+\infty} B(q)H_{-z}(q)\exp(iqr)d^2q \quad (2\text{-}2)$$

where $B(q)$ is the Fourier transform of $b(r)$, intensity of the diffracted wave in the focal plane (the intensity of the reference wave is here assumed to be constant), $H_{-z}(q)$ is the Fourier transform of $H_{-z}(r)$ and q is the dual variable of r in the Fourier transform.

It will therefore be understood that it is possible to construct a stack of images $I_1, \ldots, I_N$ for ordinates $z_1, \ldots, z_N$ along the optical axis, the origin of the ordinates being taken at the axial focus position, each image $I_n$ being defined by a complex amplitude $a(r, z_n)$.

At step 220, in the stack of images $I_1, \ldots, I_N$ obtained at the preceding step, a reference image $I_{ref}$ is selected. This reference image is the one which best corresponds to the ideal focusing conditions on the biological particles of interest. Under ideal experimental conditions, the particles are located on the inner surface 132*i* of the upper slide 132 and this surface is perpendicular to the optical axis Δ. The ideal focusing conditions are then those in which the focus plane merges with the aforementioned inner surface.

In practice, when the biological particles are not transparent, the selection of the reference image can be made in accordance with a criterion of maximum contrast applied to a region containing the biological particles. This maximum contrast criterion may be a maximum standard deviation for example, or a mean value of a maximum gradient in this region.

When the biological particles are transparent, advantageously an optical system is used having spherical aberration to avoid complete disappearance of the signal at the focusing position.

At all events, the axial position of the reference image is then taken to be the reference position (z=0), the positions of the other images in the stack being calculated in relation to this reference position.

At step 230, at least one particle to be analysed is selected in the reference image. This selection can be automated and performed for example on the basis of morphological and/or photometric criteria. For each particle to be analysed, its position (x,y) is determined in the reference image, and a region of interest is determined in the form of an image block $B_{ref}$ centred on this position. It will be noted that this bock may be of larger or smaller size than the particle to be analysed. This image block $B_{ref}$ is extracted from the reference image $I_{ref}$.

At step 240, from the other images of the stack, image blocks are extracted which correspond to the same position as the block extracted from the reference image. This gives a stack of image blocks, $B_1, \ldots, B_N$, i.e. a restriction of the stack of images to the region of interest centred on the particle to be analysed. It will be understood that each block of the stack corresponds to a different axial position and hence to different defocusing conditions in relation to the reference block $B_{ref}$.

FIG. 3 schematically illustrates a stack of images $I_1, \ldots, I_N$ and a stack of image blocks $B_1, \ldots, B_N$ centred on a particle of interest P having coordinates (x, y). The blocks here are square-shaped, but it will be understood that other block shapes can be envisaged without departing from the scope of the present invention.

Optionally, at step 250, the selection of the reference image is fine-tuned, and hence also of the reference image block for the particle to be analysed. If all the particles do not lie in one same plane orthogonal to the optical axis, which may particularly be the case when the inner surface of the upper slide is not fully orthogonal to the optical axis, the focus plane may differ from one particle to another. A search is then made among the blocks of the stack, and advantageously among the image blocks either side of the reference image $I_{ref}$ selected at step 220, for the one which best corresponds to the focusing conditions. This selection can be carried out, as at step 220, using a criterion of maximum contrast but this time on the blocks of the stack. The maximum contrast criterion here too may be a maximum standard deviation or a mean value of a maximum gradient on the block. The block selected then becomes the new reference block, $B_{ref}$, of the stack.

FIG. 4 illustrates an example of a search for a reference block in a stack of image blocks of a biological particle. The subscripts of the blocks are given along the X-axis, each block $B_n$, corresponding to a different axial position $z_n$, and the standard deviation of intensity of the pixels in the block is given along the Y-axis.

The search for a reference image, $I_{ref}$ at step 220 and the extraction of the block centred on the particle of interest at step 230 gives a first reference block designated as $B_{ref}^{(1)}$ in the Figure. The more fine-tuned search for focus at optional step 250 gives a second reference block, $B_{ref}^{(2)}$, corresponding to the maximum of the standard deviation curve. If this step is performed, it is therefore this second reference block which will be taken to be the reference block, $B_{ref}$, for the remainder of the identification method.

At step 260, at least one characteristic magnitude $G(z_n)$ is calculated for each block $B_n$ of the stack of blocks, and an axial profile is inferred of this characteristic magnitude, along the optical axis. More specifically, if the blocks $B_1, \ldots, B_N$ correspond to axial positions $z_1, \ldots, z_N$, the block axial profile is composed of the sequence $G(z_1)$, $G(z_2), \ldots G(z_N)$.

This characteristic magnitude may notably a statistical magnitude related to the block, for example a mean, median, standard deviation of intensity of the pixels in the block. In addition, if the images of the stack have been obtained by numerical propagation and not experimentally acquired, a complex value can be associated with each pixel of the block. The characteristic magnitude may then concern the real part or imaginary part of these complex values. For example, as characteristic magnitude it is possible to take the square of the mean value of the imaginary part of the complex amplitude in the block, i.e. for block $B_n$:

$$G(z_n) = E[|\Im(a(r;z_n))|^2] \quad (3)$$

where $E(.)$ designates the mean relative to $r \in B_n$.

Optionally, the discrete values $G(z_1), G(z_2), \ldots G(z_N)$ can be interpolated to obtain more fine-tuned resolution of the profile of the characteristic magnitude.

At step 270, the type of biological particle is identified from the axial profile thus obtained.

According to a first, particularly simple variant, the axial profile $G(z)$ can be compared with a threshold value and discrimination obtained between two types of particles.

Figure 5A:
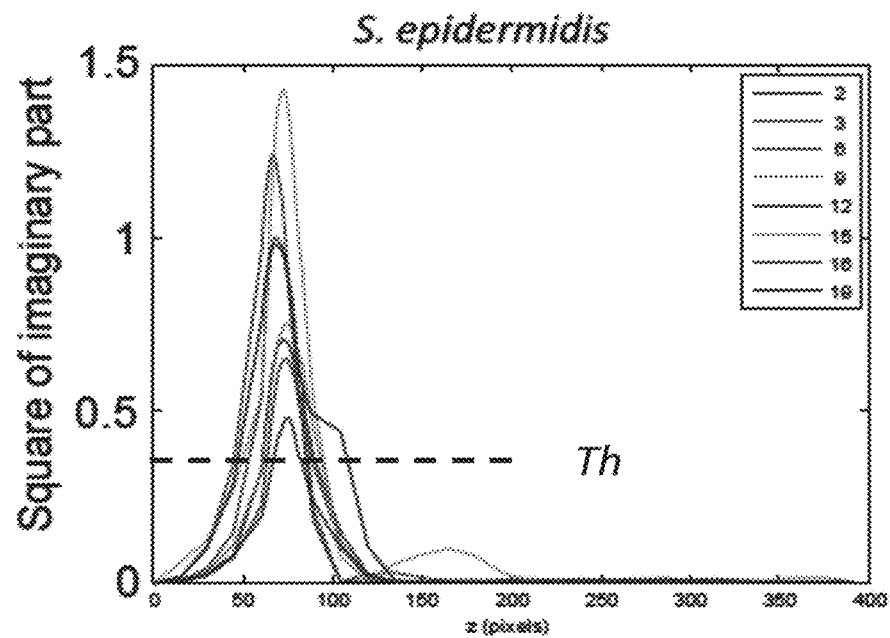
FIGS. 5A and 5B illustrate axial profiles of a characteristic magnitude of two known types of biological particles respectively.
Figure 5B:
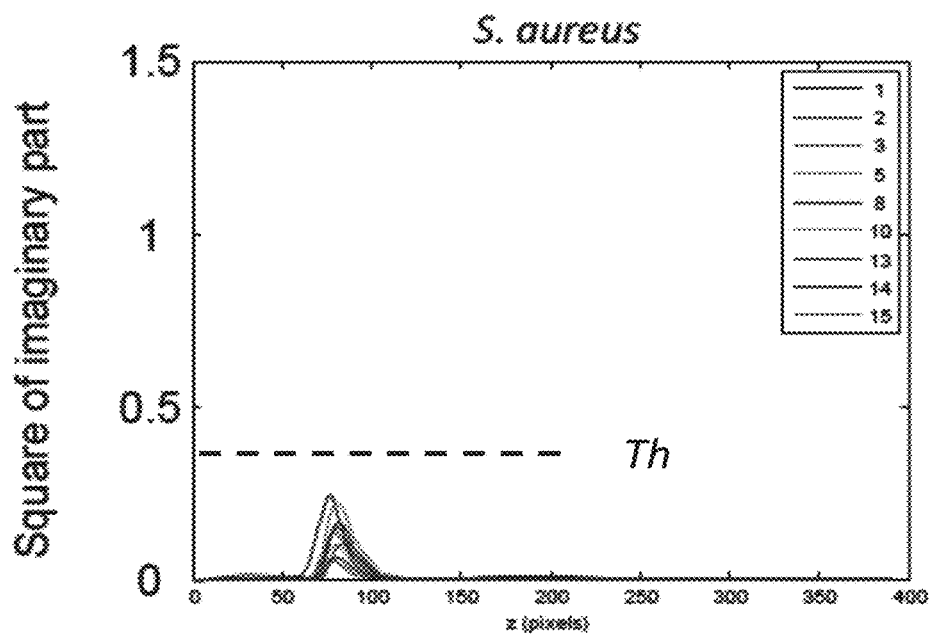

FIGS. 5A and 5B illustrate the axial profiles of a characteristic magnitude (here the square of the mean value of the imaginary part of the amplitude in the block) for two types of biological particles, namely *Staphylococcus epidermidis* (FIG. 5A) and *Staphylococcus aureus*. It can be seen here that a threshold value, Th such as 0.4 allows efficient discrimination between the two types of biological particles (here two types of staphylococci). If the axial profile exceeds this threshold value, the biological particle will be identified as *S. epidermidis*, whereas if not does not exceed this threshold it will be identified as *S. aureus*.

It will be noted that this first variant does not require precise determination of the reference block $B_{ref}$. However, the reference image $I_{ref}$ must be searched to select the particle to be analysed at step 230.

In a second variant, the axial profile of the characteristic magnitude is compared, using a similarity criterion, with axial profiles of this same characteristic magnitude previously obtained for biological particles of known type, $G_1(z), \ldots G_K(z)$, stored in a database for example. The profiles $G_1(z), \ldots G_K(z)$ are denoted standard profiles. The fact that a common origin is used (reference block) facilitates comparison.

The similarity criterion may be an intercorrelation value for example or a Pearson coefficient. The subscript $k_{max} \in \{1, \ldots K\}$ for which the standard profile $G_k(z)$ is the closest to profile $G(z)$ gives the type of the biological particle.

In a third identification variant, at step 270 several characteristic magnitudes $G^l(z_n)$ $l=1, \ldots, L$ are calculated for each block $B_n$ in the stack. This gives a plurality of axial profiles $G^l(z)$ characterizing the particle. This plurality of profiles can be compared, using a similarity criterion, with a same plurality of profiles obtained for each of the K particles of known type, i.e. $G_k^l(z_n)$ $l=1, \ldots, L$, $k=1, \ldots, K$. Using a similarity criterion, the determination is made of the plurality of standard axial profiles $G_{kmax}^l(z)$ that is closest to the measured profiles. As in the first variant, the subscript $k_{max}$ gives the type of biological particle analysed.

In a fourth variant, identification of the particle uses a supervised learning method. This variant assumes the prior acquisition of axial profiles for a plurality K of types of biological particles. The biological particles are then classified in K classes using as descriptor the values of the axial profile or preferably a characteristic of this profile, each class being able to be represented by a group of dots in an L-dimensional space.

From the axial profile of a biological particle to be analysed, the corresponding dot in the L-dimensional space is determined and a search is made for the group of dots i.e. the class to which it belongs.

For example, if the magnitude defined by the expression (3) is taken to be the characteristic magnitude of a block, and its maximum value as profile characteristic, it was able to be shown that it is possible to obtain efficient classification of the bacteria *Acinetobacter johnsonii, Enterobacter aerogenes, Escherichia coli* and *Staphylococcus epidermidis*. Therefore, on samples of known populations, the following confusion matrix was obtained:

$$CM = \begin{pmatrix} 139 & 24 & 52 & 4 \\ 23 & 188 & 91 & 16 \\ 16 & 54 & 260 & 1 \\ 7 & 8 & 4 & 174 \end{pmatrix}$$

wherein the different rows correspond to populations of different types and the columns correspond to classes predicted by the identification method. It will be noted that the confusion matrix is diagonally dominant and that therefore the rate of identification error is relatively low.

Persons skilled in the art will understand that the usual supervised learning methods such as Bayesian classification techniques or support vector machines can be used to classify biological particles from their axial profiles.

FIG. 6 schematically illustrates a flowchart of the method for identifying biological particles according to a second embodiment of the invention.

The second identification method of the invention is also based on a stack of image blocks centred on the biological particle of interest. The blocks are extracted from a stack of acquired or calculated images as previously described. More specifically, steps 610 to 650 are identical to steps 610 to 650 respectively of the identification method according to the first embodiment of the invention. They will therefore not be further described.

However, at step 660 a characteristic magnitude is not calculated, but in the stack of blocks a sub-plurality M of blocks is selected positioned at predetermined deviations ($en_z$) relative to the reference block, $B_{ref}$ ($z=0$). In practice, the images of the stack being acquired or calculated (by numerical propagation) at regular intervals, the selection from the stack of blocks will concern predetermined subscripts relative to the subscript of the reference block.

At step 670, using a similarity criterion, the M-tuple of selected blocks is compared with M-tuples of standard blocks, each M-tuple of standard blocks relating to a biological particle of known type, the blocks of each M-tuple themselves having been obtained at the aforementioned predetermined distances.

The similarity criterion may be a spatial correlation, a Pearson coefficient, a quadratic deviation between a Fourier transform of the blocks of the particle to be analysed and a transform of standard blocks, and can even be based on principal component analysis (PCA). In this latter case, for each block of the M-tuple of blocks of the particle to be analysed and each block of the M-tuple of standard blocks, the main axes of pixel distribution can be determined and a comparison made (e.g. with a scalar product of direction vectors) between the alignment of the main axes of the blocks of the particle to be analysed with the main axes of the standard blocks.

Irrespective of the chosen similarity criterion, the M-tuple of standard blocks the closest to the M-tuple of blocks of the particle to be analysed, at step 680 gives the type of the biological particle.

Figure 7:
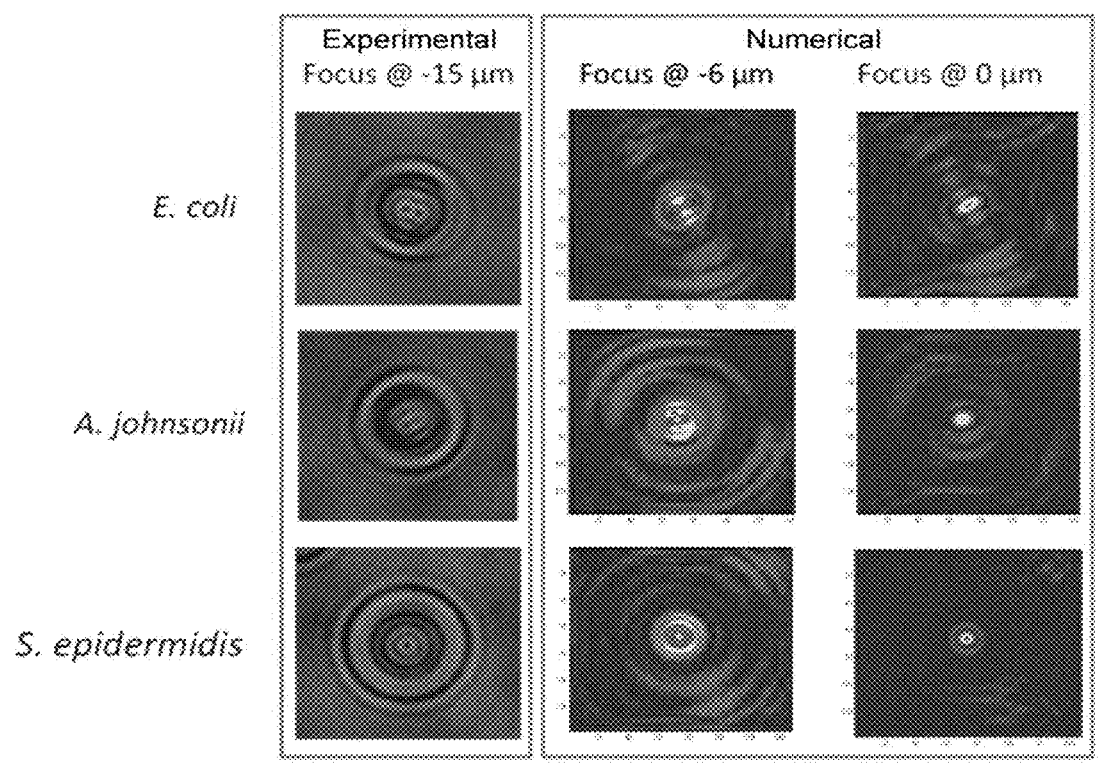
FIG. 7 gives an example of M-tuples of standard blocks for different known types of biological particles.

FIG. 7 gives an example of an M-tuple of standard blocks for different biological particles.

In the illustrated case, M=3 and the predetermined defocusing deviations are respectively 15 μm (image blocks in the $1^{st}$ column), 6 μm (image blocks in the $2^{nd}$ column) and 0 µm (image blocks in the 3$^{rd}$ column in the focus plane), the deviations being calculated positively in the direction of propagation of the beam.

The standard blocks in the first row relate to the species *E. coli*, the standard blocks in the second row relate to the species *A. johnsonii* and the standard blocks in the third row relate to the species *S. epidermidis*.

It can be seen that the standard blocks of the species *E. coli* and *A. johnsonii* have very similar structures at 15 µm whereas the standard block of *S. epidermidis* has a much different structure. Similarly, the standard blocks of the species *A. johnsonii* and *S. epidermidis* have very similar structures at 0 µm, whereas *E. coli* has a much different structure. The use of a triplet of image blocks therefore allows the lifting of identification ambiguity.

The invention claimed is:

1. A method for identifying biological particles from a stack of holographic images obtained by means of an optical system, the method comprising;
    obtaining said holographic images for a plurality of defocusing deviations relative to a focus plane, the defocusing deviations being taken along an optical axis of the optical system;
    selecting a reference holographic image in the stack of holographic images as being an image closest to the focus plane;
    selecting an image block from the reference holographic image, the selected image block including a biological particle of interest;
    extracting from the holographic images other than the reference holographic image, a stack of image blocks corresponding to a position of the selected image block within the reference holographic image;
    identifying a type of the biological particle of interest from the extracted stack of image blocks.

2. The method for identifying biological particles according to claim 1, wherein the holographic images are acquired by the optical system for a plurality of positions along the optical axis of the optical system.

3. The method for identifying biological particles according to claim 1, wherein a first holographic image is acquired by the optical system, wherein other holographic images of the stack of holographic images are calculated from the first holographic image using a numerical propagation model.

4. The method for identifying biological particles according to claim 3, wherein the first holographic image is taken with non-zero defocusing deviation relative to the focus plane.

5. The method for identifying biological particles according to claim 1, wherein said reference holographic image is selected from the stack of holographic images as an image that maximises a predetermined contrast criterion.

6. The method for identifying biological particles according to claim 5, wherein the selected image block is an image block centred on the biological particle of interest within the reference holographic image, a position of the selected image block on the optical axis of the optical system then being selected as origin for defocusing deviations.

7. The method for identifying biological particles according to claim 6, wherein the selected image block is updated by searching, among other image blocks centred on the biological particle of interest and belonging to neighbouring images of the reference holographic image in the stack of holographic images, for an image block of the other image blocks that maximises a predetermined contrast criterion.

8. The method for identifying biological particles according to claim 1, further comprising
    calculating, for each block of the stack of image blocks, a value of at least one characteristic magnitude, and
    obtaining a profile of said characteristic magnitude along the optical axis of the optical system from the calculated values of the characteristic magnitude.

9. The method for identifying biological particles according to claim 8, further comprising
    comparing the profile of said characteristic magnitude with a threshold, and
    identifying that the biological particle of interest is of a first type if the profile exceeds the threshold and that the biological particle of interest is of a second type if the profile does not exceed the threshold.

10. The method for identifying biological particles according to claim 8, further comprising
    comparing, by using a similarity criterion, the profile of said characteristic magnitude with a plurality of standard profiles obtained for different known types of biological particles, and
    identifying the type of the biological particle of interest from a standard profile of the plurality of profiles having a greatest similarity with the profile of said characteristic magnitude.

11. The method for identifying biological particles according to claim 10, wherein the similarity criterion is selected from among an intercorrelation, a Pearson coefficient, and a quadratic deviation.

12. The method for identifying biological particles according to claim 8, further comprising classifying the profile of said characteristic magnitude using a supervised learning method among a plurality of classes of profiles, each class corresponding to a given type of biological particle.

13. The method for identifying biological particles according to claim 6, further comprising selecting, from said stack of image blocks, a plurality of blocks corresponding to predetermined defocusing deviations.

14. The method for identifying biological particles according to claim 13, further comprising
    comparing, using a similarity criterion, said plurality of selected blocks, with pluralities of standard blocks, each plurality of standard blocks corresponding to a given type of biological particle, and
    identifying the type of the biological particle of interest from the plurality of standard blocks having a greatest similarity with said plurality of selected blocks.

15. The method for identifying biological particles according to claim 14, wherein the similarity criterion is at least one of an intercorrelation, a quadratic deviation, quadratic deviation after spatial Fourier transform, or a criterion based on principal component analysis.

16. A method for identifying biological particles from a stack of holographic images obtained by means of an optical system, the method comprising:
    obtaining said holographic images for a plurality of defocusing deviations relative to a focus plane, the defocusing deviations being taken along an optical axis of the optical system;
    selecting a reference holographic image in the stack of holographic images as being an image closest to the focus plane;
    for a biological particle of interest, extracting from the stack of holographic images a stack of image blocks comprising said biological particle of interest;
    selecting, from the extracted stack of image blocks, a reference block as an image block centred on the biological particle of interest within the reference holographic image, a position of the reference block on the optical axis then being selected as origin for defocusing deviations;

updating the selected reference block by searching, among other image blocks centred on the biological particle of interest and belonging to neighbouring images of the reference holographic image in the stack of holographic images, for an image block of the other image blocks that maximises a predetermined contrast criterion; and identifying a type of the biological particle of interest from the extracted stack of image blocks.

\* \* \* \* \*

UNITED STATES PATENT AND TRADEMARK OFFICE
CERTIFICATE OF CORRECTION

PATENT NO. : 10,458,897 B2
APPLICATION NO. : 15/536507
DATED : October 29, 2019
INVENTOR(S) : Francois Perraut et al.

Page 1 of 1

It is certified that error appears in the above-identified patent and that said Letters Patent is hereby corrected as shown below:

On the Title Page

Item (72), the third inventor's city is incorrect. Item (72) should read:
-- (72) Inventors: Francois Perraut, Saint Joseph de Riviere (FR); Pierre Joly, Grenoble (FR); Quentin Josso, Lyon (FR); Meike Kloster-Landsberg, Grafelfing (DE); Alice Douet, Grenoble (FR) --

Signed and Sealed this
Thirty-first Day of December, 2019

Andrei Iancu
*Director of the United States Patent and Trademark Office*